(12) United States Patent  (10) Patent No.: US 9,339,340 B2
Golden et al.  (45) Date of Patent: May 17, 2016

(54) MEDICAL INSTRUMENT GUIDING DEVICE WITH AN INTEGRATED GUIDE BALL

(71) Applicant: Lucent Medical Systems, Inc., Kirkland, WA (US)

(72) Inventors: Robert N. Golden, Kirkland, WA (US); Curtis S. King, Kirkland, WA (US)

(73) Assignee: Lucent Medical Systems, Inc., Kirkland, WA (US)

( * ) Notice: Subject to any disclaimer, the term of this patent is extended or adjusted under 35 U.S.C. 154(b) by 320 days.

(21) Appl. No.: 13/857,847

(22) Filed: Apr. 5, 2013

(65) Prior Publication Data

US 2013/0267963 A1 Oct. 10, 2013

Related U.S. Application Data

(60) Provisional application No. 61/620,884, filed on Apr. 5, 2012.

(51) Int. Cl.
*A61B 19/00* (2006.01)
(52) U.S. Cl.
CPC .................................. *A61B 19/201* (2013.01)
(58) Field of Classification Search
CPC ............ A61B 17/3403; A61B 19/201; A61B 17/1703; A61B 17/1717; A61B 17/1721
USPC ................. 606/129, 130; 604/164.01–170.03
See application file for complete search history.

(56) References Cited

U.S. PATENT DOCUMENTS

| 5,263,956 | A | * | 11/1993 | Nobles | 606/130 |
| 5,658,272 | A | * | 8/1997 | Hasson | 606/1 |
| 7,153,257 | B2 | * | 12/2006 | Schneider et al. | 600/25 |
| 7,241,298 | B2 | * | 7/2007 | Nemec | A61B 17/15 606/86 R |
| 2003/0055436 | A1 | * | 3/2003 | Daum | A61B 19/201 606/130 |
| 2004/0267284 | A1 | * | 12/2004 | Parmer | A61B 19/201 606/130 |
| 2010/0249497 | A1 | * | 9/2010 | Peine et al. | 600/104 |

* cited by examiner

*Primary Examiner* — Gregory Anderson
*Assistant Examiner* — Erich Herbermann
(74) *Attorney, Agent, or Firm* — Seed IP Law Group PLLC

(57) ABSTRACT

A medical instrument guiding device includes a body base component, and a guide body upper component assembled to the body base component. The guide body upper component has a substantially semi-spherical shape to house a medical instrument guide ball resting on a friction surface located within the body base component. The surface of the guide body upper component includes a cut out working area, and a surface of the medical instrument guide ball is exposed by the cut out working area. A medical instrument port is arranged on a truncated surface of the medical instrument guide ball, and a medical instrument may be passed through the medical instrument port. The medical instrument guide ball permits the medical instrument to be moved in three dimensions. The medical instrument port permits the medical instrument to be advanced into a patient.

18 Claims, 10 Drawing Sheets

MEDICAL INSTRUMENT GUIDING DEVICE WITH AN INTEGRATED GUIDE BALL

CROSS-REFERENCE TO RELATED APPLICATION

This application claims the benefit under 35 U.S.C. §119 (e) of U.S. Provisional Patent Application No. 61/620,884 filed Apr. 5, 2012, where this provisional application is incorporated herein by reference in its entirety.

BACKGROUND

1. Technical Field

The present disclosure generally relates to medical instruments and more particularly but not exclusively relates to guiding devices for the placement of medical instruments into the body of a patient.

2. Description of the Related Art

In many medical situations, it is desirable to penetrate the solid or semi-solid biological matter of a patient's body and guide a medical instrument to a precise location. For example, one common medical practice involves diagnosis and therapy of a tumor in a patient's body. Another common medical practice involves accurately placing a needle in a patient's body. Various mechanical guiding systems are available to help medical practitioners guide medical instruments into the internal anatomy and structures of a patient. Mechanical guidance systems for medical instruments function to help medical practitioners diagnose, treat, and provide care to patients.

It is common in various clinical procedures to use a stereotactic apparatus to position a device or instrument at specified orientation and location relative to a target area on a body or specimen. These known types of devices exist in many form factors. Some are independent mechanisms that integrate with a specific device or tool set, and others are physical features built into an instrument. All are designed to allow controlled manipulation of a device in a designated geometric reference plane, or multiple reference planes.

The physical nature of some of known devices results in a restricted geometric range of motion, and it may be difficult or impossible under certain conditions to achieve and maintain a desired position of the instrument. In the case of a fixed needle guide, where a user is limited to motion in a single plane at a fixed angle, it may be necessary to switch between multiple guide geometries during a procedure to achieve proper needle position. Difficulty in positioning the needle increases the overall complexity of the procedure. Extra setup steps can increase the duration of a procedure, which may negatively impact the health of the patient.

BRIEF SUMMARY

The present embodiments provide new procedures and devices that provide more accurate placement of medical instruments into the body of a patient.

The present inventive device is embodied in a ball-type, swiveling joint apparatus with an integrated device clamp or retaining port that allows for the axial advancement of a surgical device through the port, with simultaneous, stereotactic manipulation via the ball rotation.

The device is analogous to a ball joint with a fixed bearing housing and movable ball. The ball is able to rotate unobstructed within the housing, which is fixed either temporarily or permanently, to a secondary surface or plane. The ball surface incorporates a clamp or port through which a needle or other device can be passed. The friction between the device and the clamp or port is sufficient for the retention of the tool in the housing in the absence of an external force. Furthermore, the design of the friction fit between the ball and housing keeps the ball (and device) in a fixed orientation until the user forcibly manipulates the device. The fit characteristics provide tactile feedback to the user, which when coupled with the device retention, simplify the overall positioning process and eliminate the need for either multiple fixtures for a range of positions, or devices with limited ranges of motion. The device, therefore provides a stereotactic fixture incorporating a ball-type joint mounted to, or incorporated on, an external instrument providing for retention and full range (3D) kinematic adjustment of a needle or other device during a surgical procedure.

BRIEF DESCRIPTION OF THE SEVERAL VIEWS OF THE DRAWINGS

Non-limiting and non-exhaustive embodiments are described with reference to the following drawings, wherein like labels refer to like parts throughout the various views unless otherwise specified. The sizes and relative positions of elements in the drawings are not necessarily drawn to scale. One or more embodiments are described hereinafter with reference to the accompanying drawings in which.

DETAILED DESCRIPTION

There exists a need in the medical arts for an apparatus that will provide full range kinematic adjustability and secure retention of a medical instrument during a surgical procedure.

A medical instrument is a device used in a procedure on the body of a patient. Medical instruments include needles, probes, rigid tubes, and other like apparatus. Medical instruments are used on patients in surgery, preventive care, diagnosis of disease or other condition, and a wide range of physiological processes. Some medical instruments have passages to pass light, fluid, or other therapies. Other medical instruments are solid and pass electricity or mechanical force (e.g., a probe used by a medical practitioner to move or sample a biological mass).

Figure 1:
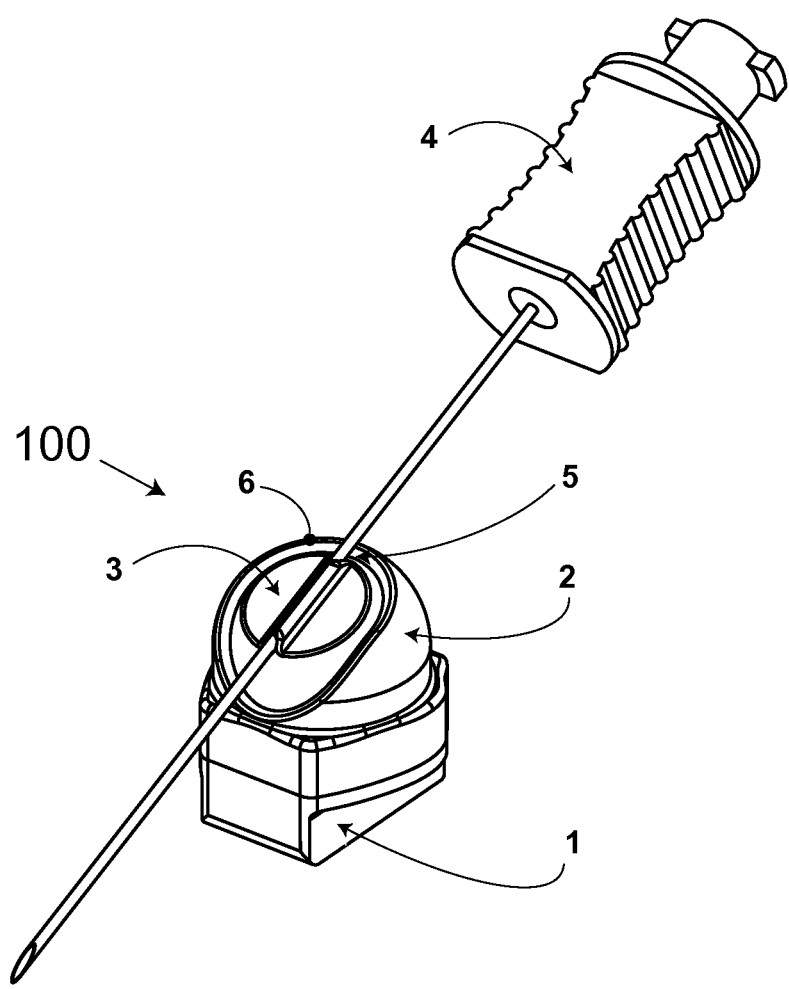
FIG. 1 illustrates one embodiment of a stereotactic fixture incorporating a ball-type joint mounted to, or incorporated on, an external instrument.

FIG. 1 illustrates one embodiment of a stereotactic fixture incorporating a ball-type joint mounted to, or incorporated on, an external instrument. Embodiments of the present invention are medical instrument guiding devices having an integrated guide ball 100. The embodiment provides for retention and wide range, three dimensional kinematic adjustment of a needle or other medical instrument during a surgical procedure. The embodiment includes a ball-type, swiveling joint apparatus with an integrated device clamp or retaining port that allows for the axial advancement of the medical instrument through the port, with simultaneous, stereotactic manipulation via the ball's rotation.

The medical instrument guiding device having an integrated guide ball 100 of FIG. 1 includes a medical instrument guide body base component 1. The body base component 1 includes features on the underside for connecting a medical instrument guide assembly to a support surface or to a secondary plane. The body base component 1 also includes a bearing surface for ball rotation.

A guide body upper component 2 is coupled (e.g., snap fit) to the body base component 1. In addition, or as an alternative, the guide body upper component 2 may be welded, glued, or otherwise affixed to the body base component 1. The guide body upper component 2 includes a bearing surface and a surface defining a translation area for a fixture.

The medical instrument guiding device having an integrated guide ball 100 includes a medical instrument guide ball 3. The medical instrument guide ball 3 includes a port 5 to retain the medical instrument.

In FIG. 1, the medical instrument guiding device having an integrated guide ball 100 is illustrated with a representative medical instrument 4. The medical instrument 4 in FIG. 1 is a needle; however, other types of medical instruments may also be used. The needle 4 can be advanced axially through the port 5, rotated, and the distal tip can be moved in three dimensions.

The needle 4 of FIG. 1 is illustrated having a handle of approximately the same size as the medical instrument guiding device having an integrated all-joint 100, but smaller or larger medical instruments could also be used. Furthermore, the size of the components of the medical instrument guiding device having an integrated guide ball 100 can be easily scaled to accommodate smaller or larger medical instruments.

In the medical instrument guiding device having an integrated guide ball 100 of FIG. 1, a workable area 6 provides a definition of travel for the medical instrument. The workable area 6 can be adjusted as necessary to achieve a required functional range of motion.

In the embodiment of FIG. 1, the ball joint is assembled with a fixed bearing housing 2 and movable ball 3. The ball 3 is able to rotate unobstructed within the housing 2, which is fixed either temporarily or permanently, to a secondary surface or plane 1. The ball 3 surface includes a port 5 through which a medical instrument 4 can be passed. The friction between the medical instrument 4 and the port 5 is sufficient for the retention of the medical instrument 4 in the housing 2 in the absence of an external force. Furthermore, the design of the friction fit between the ball 3 and housing 2 keeps the ball 3 and the medical instrument 4 in a fixed orientation until the medical practitioner uses some force to manipulate the medical instrument 4. The fit characteristics provide tactile feedback to the medical practitioner, which when coupled with the device retention, simplify the overall positioning process and eliminate the need for multiple fixtures for a range of positions and conventional devices having limited ranges of motion.

Figure 2:
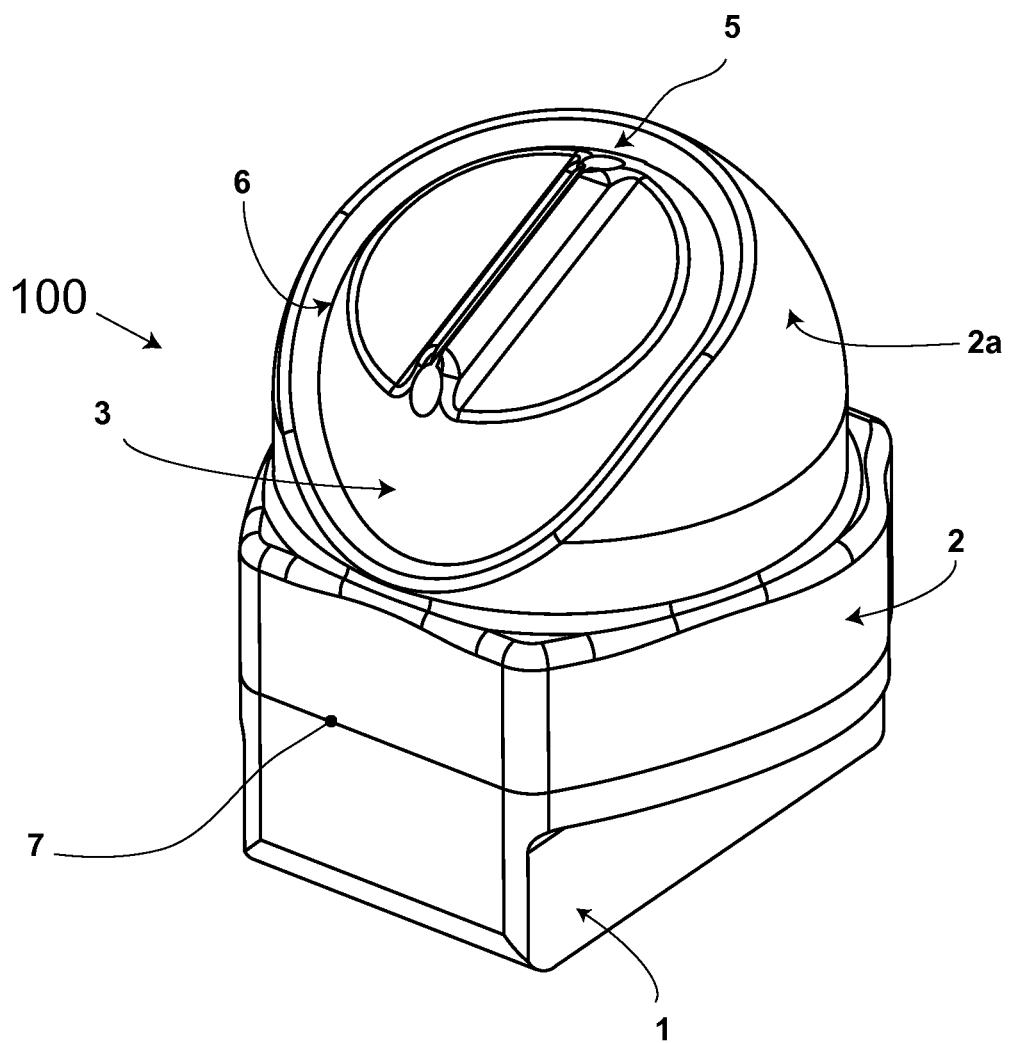
FIG. 2 illustrates close up view of a medical instrument guiding device having an integrated guide ball.

FIG. 2 illustrates close up view of a medical instrument guiding device having an integrated guide ball 100. The medical instrument body base component 1 is represented below the guide body upper component 2. In some embodiments, the mating surface 7 between the medical instrument body base component 1 and the guide body upper component 2 forms a permanent junction, and in other embodiments the mating surface 7 forms a temporary junction. For example, the mating surface 7 joint may be welded or glued. As another example, mating surface 7 joint may be snapped together or held together with screws. The surface location, proximity of the parts to each other, materials, sizes, or other features contribute to change the force or pressure on the medical instrument guide ball 3. This force or pressure is one of several forces that contribute to the rotational performance and tactile feel of the medical instrument guiding device having an integrated guide ball 100.

In the embodiment of FIG. 2, the semi-spherical housing portion 2A that retains the medical instrument guide ball 3 is illustrated as being coupled to the medical instrument guide body upper component 2. In some cases, these two distinguishable structures are integrated as a single unit, and in other cases, the semi-spherical housing portion 2A that retains the medical instrument guide ball 3 is formed separately from the body upper component 2 that is joined to the body base component 1.

Figure 3:
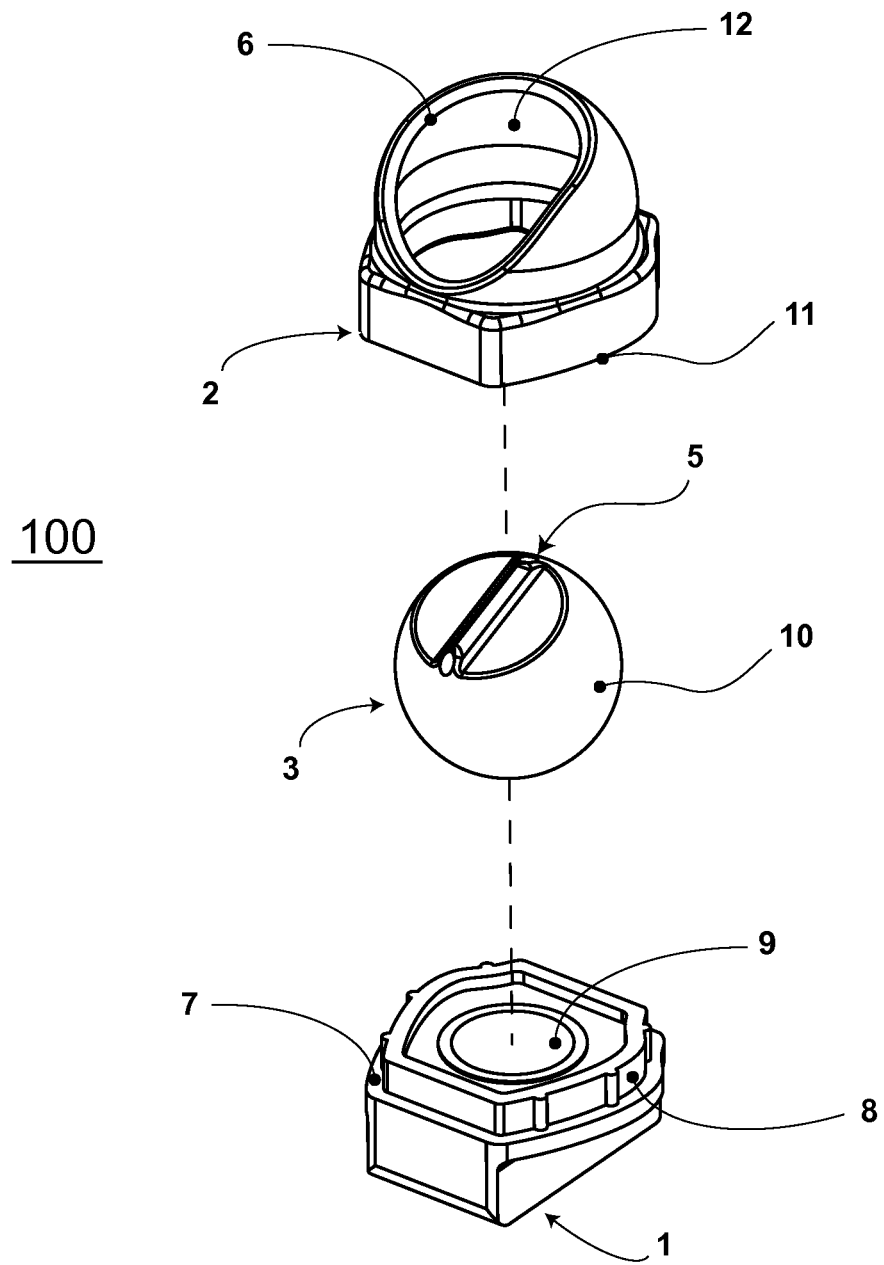
FIG. 3 illustrates an exploded view of one embodiment of a medical instrument guiding device having an integrated guide ball.

FIG. 3 illustrates an exploded view of one embodiment of a medical instrument guiding device having an integrated guide ball 100. The body base component 1 has several internal structures and features. The mating surface 7 shown in the embodiment of FIG. 3 is conducive to gluing or welding, however, other configurations of the mating surface 7 may permit different mechanisms for affixing the body base component 1 to the guide body upper component 2. A second mating surface 8 is a friction fit mechanism. The second mating surface 8 is useful to correctly guide assembly of the body base component 1 to the guide body upper component 2. Any variety of guidance protrusions, valleys, or other types of mating surfaces can be used.

The body base component 1 includes a friction surface 9 for the medical instrument guide ball 3. The friction surface 9 bears the mass of the medical instrument guide ball 3, and the friction surface 9 mates with guide ball surface 10. Pressure on the guide ball 3 when the guide body upper component is in place contributes to the force required to move the ball. The materials used to construct the medical instrument guide ball 3 and friction surface 9 also contribute to the force required to move the ball. In some cases, a lubricating agent is applied to the friction surface 9 or the guide ball surface 10. In other cases a conditioning agent is applied to the friction surface 9 to increase the friction between the guide ball 3 and the friction surface 9. Other mechanisms of controlling the force necessary to maneuver the guide ball 3 can also be used. For example, the relative size and shape of the components can be selected to increase or decrease the surface area of contact between the components. The mass of the medical instrument guide ball 3 can be selected provide the desired amount of gravitational force. This smoothness or other surface qualities can be appropriately selected, and still other modifications can be made to control the amount of force applied to move the guide ball 3.

Additional detail of the guide body upper component 2 is also illustrated in FIG. 3. An upper component mating surface 11 is cooperatively configured for assembly to the body base component mating surface 7. An upper component bearing surface 12 is configured to retain the guide ball 3 and apply further friction to the medical instrument guide ball surface 10. The sizes, materials, conditioning agents, lubricating agents, surface parameters, and the like may each be selected to control the amount of force needed to maneuver the medical instrument guide ball 3 and to provide tactile feedback. The workable area 6 of the medical instrument guiding device having an integrated guide ball 100 is shown in more detail in FIG. 3. The size, shape, and location of the opening formed by the workable area 6 direct the range of permissible movement of the medical instrument passed via the port 5. The bearing surface 12 can have one or more clamp structures therein to apply pressure to ball 3 to increase the friction and make it harder for the ball to move or to release pressure to make it easier to move.

Figure 4:
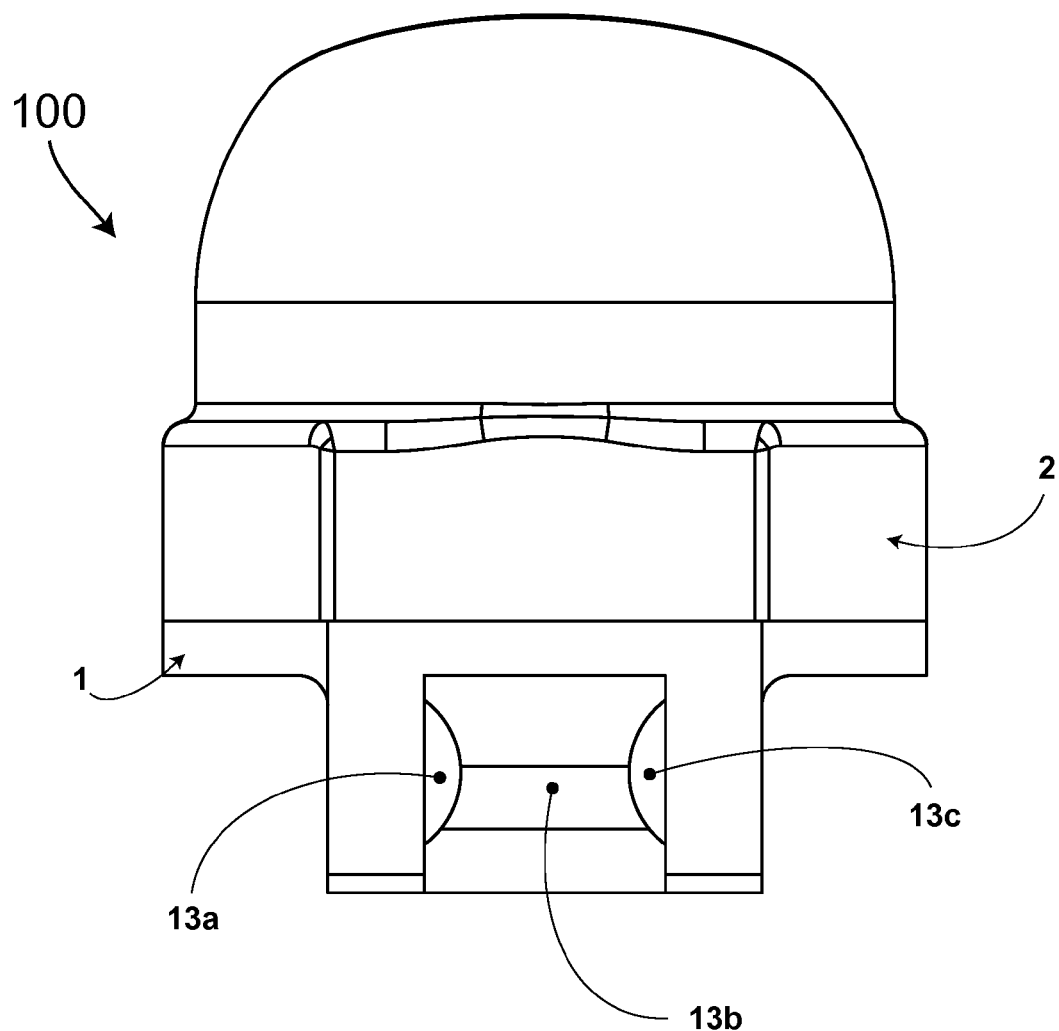
FIG. 4 illustrates a back side view of one embodiment of a medical instrument guiding device having an integrated guide ball.

FIG. 4 illustrates a back side view of one embodiment of a medical instrument guiding device having an integrated guide ball 100. The body base component 1 is attached to the guide body upper component 2. The bottom of the body base component 1 is formed having a recess that includes structures for fit and alignment of the medical instrument guiding device having an integrated guide ball 100 to a secondary instrument or surface. In the embodiment of FIG. 4, three joining structures 13a-13c are formed to permit the ball assembly 100 to be coupled to a support structure, such as a support platform or support arm placed next to the patient. The joining structures 13a-13c can be convexities or concavities, but structures of any other useful size and shape could also be selected, for example, protuberances, dimples, fractured tabs, detent mechanisms, or the like to mate with a support structure.

Figure 5:
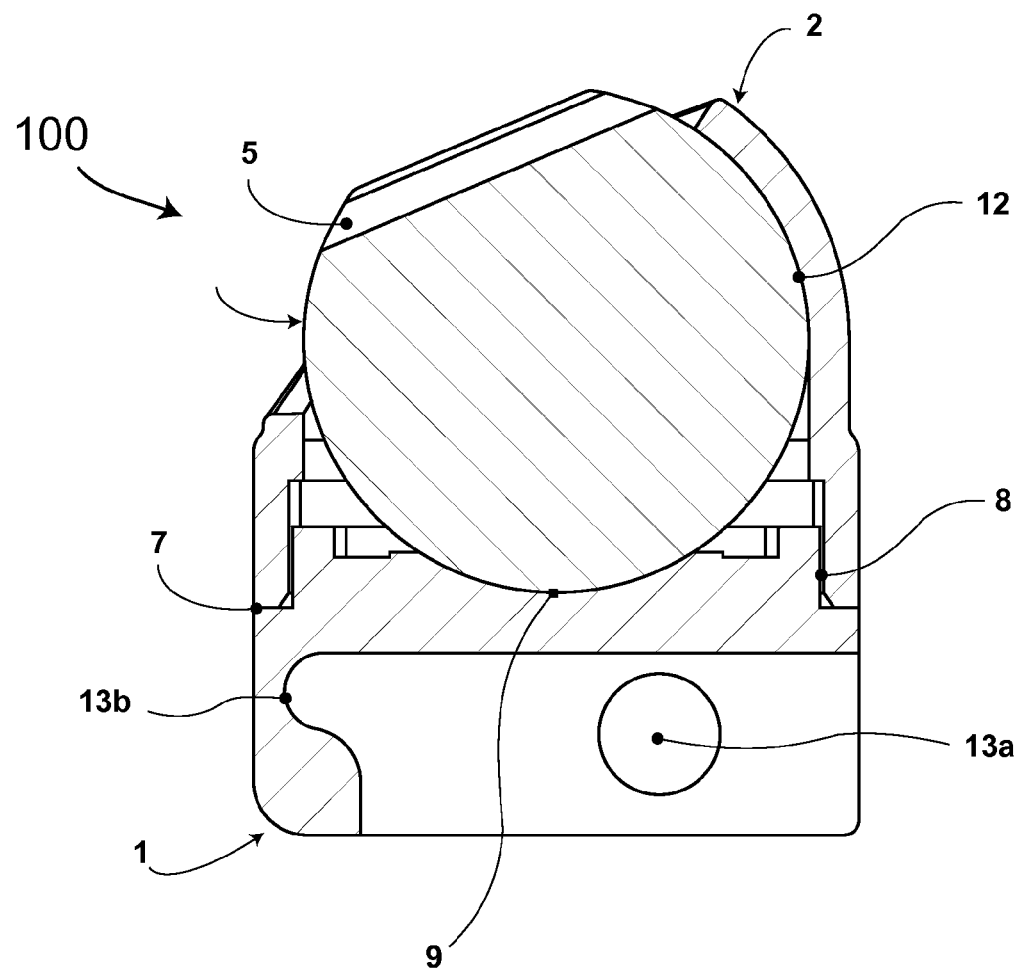
FIG. 5 illustrates a section view of one embodiment of a medical instrument guiding device having an integrated guide ball.

FIG. 5 illustrates a section view of one embodiment of a medical instrument guiding device having an integrated guide ball 100. Certain internal features of the guiding device are also shown. The body base component 1 is welded to the guide body upper component 2 along the mating surfaces 7, 8 in the embodiment of FIG. 5.

Figure 6:
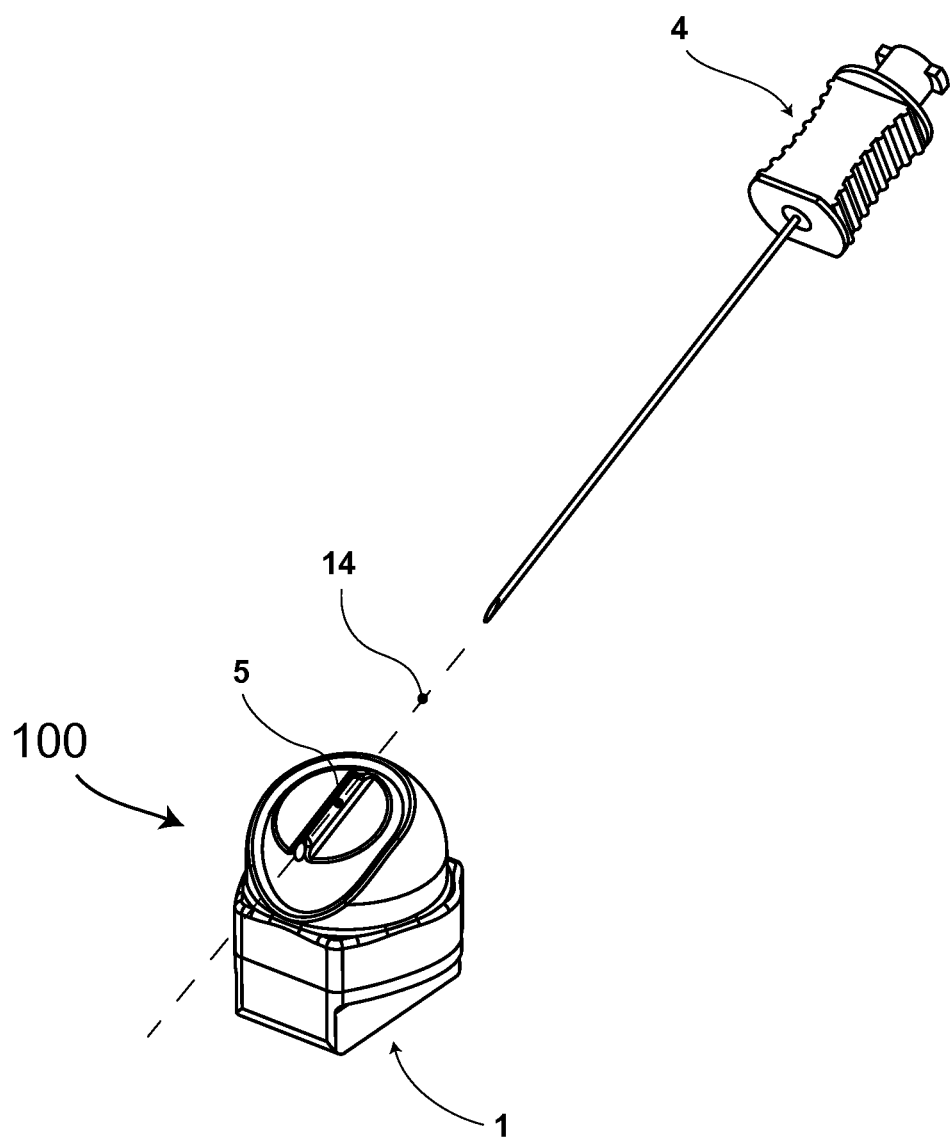
FIG. 6 illustrates a first medical instrument insertion embodiment.

FIG. 6 illustrates a first medical instrument insertion embodiment. A medical instrument guiding device having an integrated guide ball 100 is configured to receive a medical instrument 4. The medical instrument 4 is removably inserted into the guiding device 100 on an axial line 14.

Figure 7:
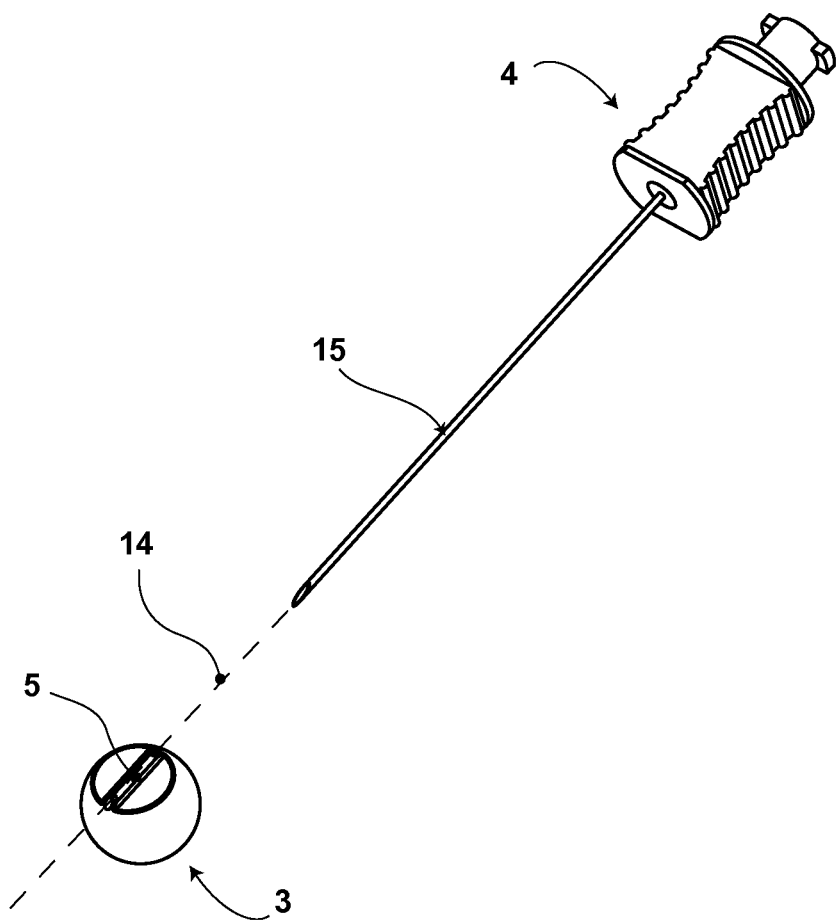
FIG. 7 illustrates a second medical instrument insertion embodiment.

FIG. 7 illustrates a second medical instrument insertion embodiment. In FIG. 7, only the medical instrument guide ball portion of the medical instrument guiding device having an integrated guide ball 100 is shown. The port 5 of the medical instrument guide ball 3 is configured to receive a needle portion 15 of a medical instrument 4 along an axial line 14.

Figure 8:
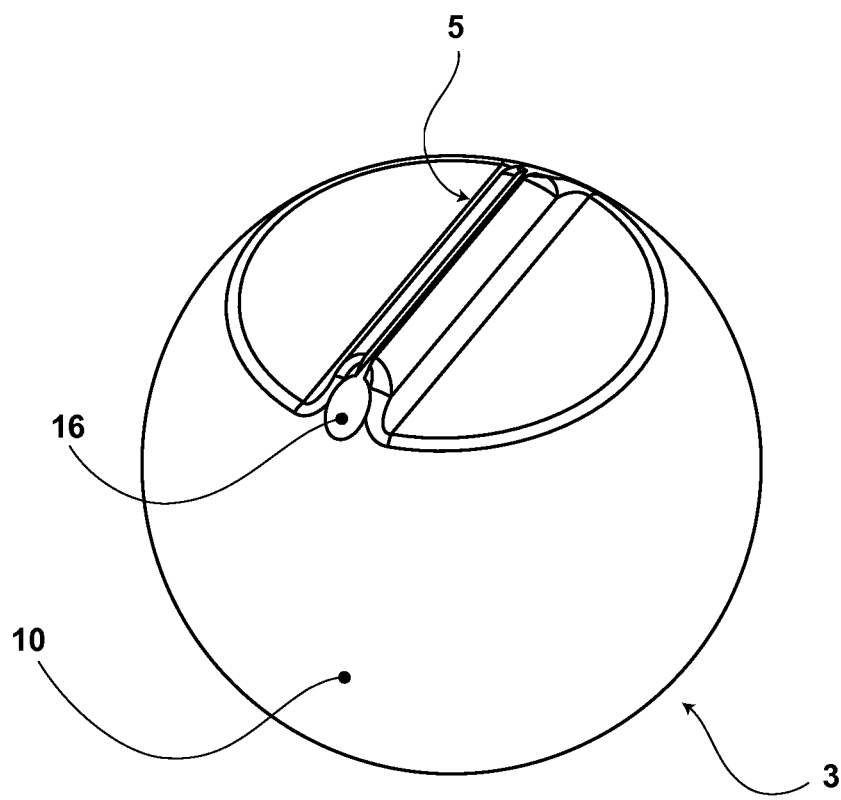
FIG. 8 illustrates a close in view of a medical instrument guide ball.

FIG. 8 illustrates a close in view of a medical instrument guide ball 3. The medical instrument guide ball surface 10 is illustrated as having a smooth, spherical composition; however, other shapes and surface formations are possible. For example, in some cases, the medical instrument guide ball 3 has substantially spherical portions, but in other cases the guide ball portion may be formed differently. Some portion of the guide ball may be truncated. The truncated portion may be within the body base component 1 or guide body upper component 2 and not visible when the guiding device 100 is assembled. In addition, or as an alternative, a truncated portion of the guide ball 3 may be formed as a planar surface on which to integrate or mount the port 5. A guide ball 3 that is slightly out of round may provide other properties useful to control the amount of force necessary to maneuver the ball. In the embodiment of FIG. 8, the port 5 is illustrated with a medical instrument clamping structure 16. In some cases, the port 5 and integrated clamping structure 16 form a channel having a selected size that completely bisects the guide ball 3. The selected size of the clamping structure channel 16 provides a desired level of friction to a medical instrument that passes through the channel. In some cases, the clamping structure 16 forms a segmented channel, which is useful to provide a desired level of friction. In still other cases, the clamping structure 16 may provide a pathway for a medical instrument that is biased in a closed orientation. In such an embodiment, a medical instrument that is passed through the clamping structure 16 spreads open the clamping structure 16 while still permitting a desired level of friction.

The clamping structure 16 may be formed from any selected materials and may take a selected shape or configuration that provides the desired friction to a medical instrument moving axially through the port 5. A conditioning agent to increase or decrease the level of friction may be applied to the clamping structure 16. In some cases, the clamping structure may have a manually adjustable feature to permit a medical practitioner to adjust the level of friction applied to a medical instrument.

Figure 9:
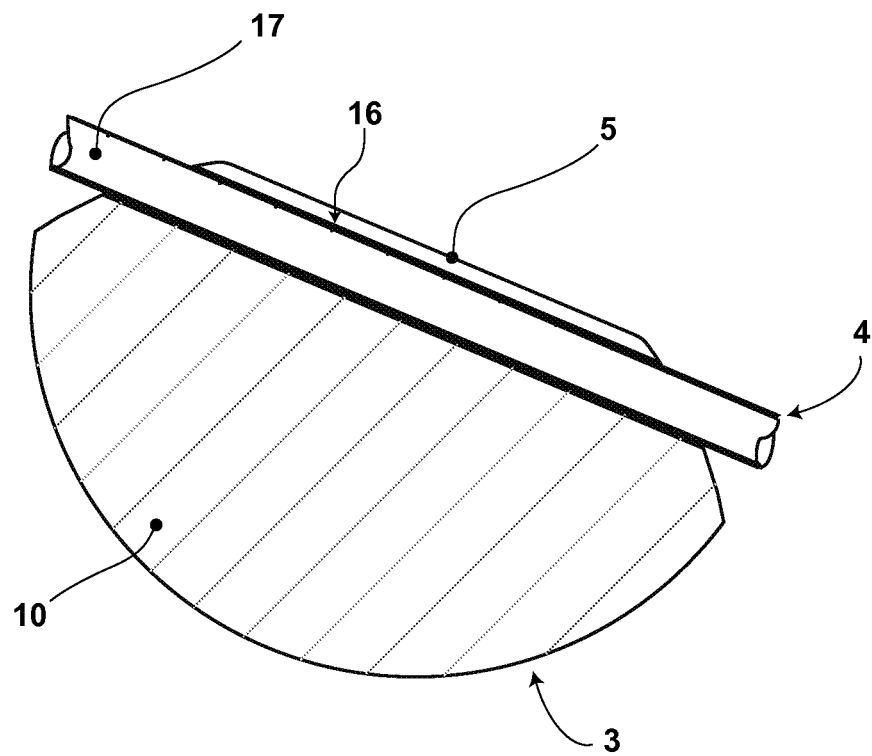
FIG. 9 illustrates a cross-sectional view of a medical instrument guide ball embodiment with a medical instrument passing through a port.

FIG. 9 illustrates a cross-sectional view of a medical instrument guide ball 3 embodiment with a medical instrument 4 passing through port 5. In the embodiment, the medical instrument surface 17 is in contact with the clamping structure 16 of the port 5. A conditioning agent may or may not be applied. In some cases, the port 5 and clamping structure 16 are integrally formed simply by forming (e.g., drilling) a hole of a selected size through the medical instrument guide ball 3. In such a case, the port 5 of FIG. 9 is part of the medical instrument guide ball surface 10, and the clamping structure 16 is the inner surface area of the channel formed in (e.g., drilled through) the guide ball 3. In other cases, the port 5 may be formed or affixed on a truncated top portion of the guide ball 3. Constructing the guiding device 100 with such a truncated upper portion of a guide ball 3 may permit any one of several types of port to be integrated with the same guide ball 3.

Figure 10:
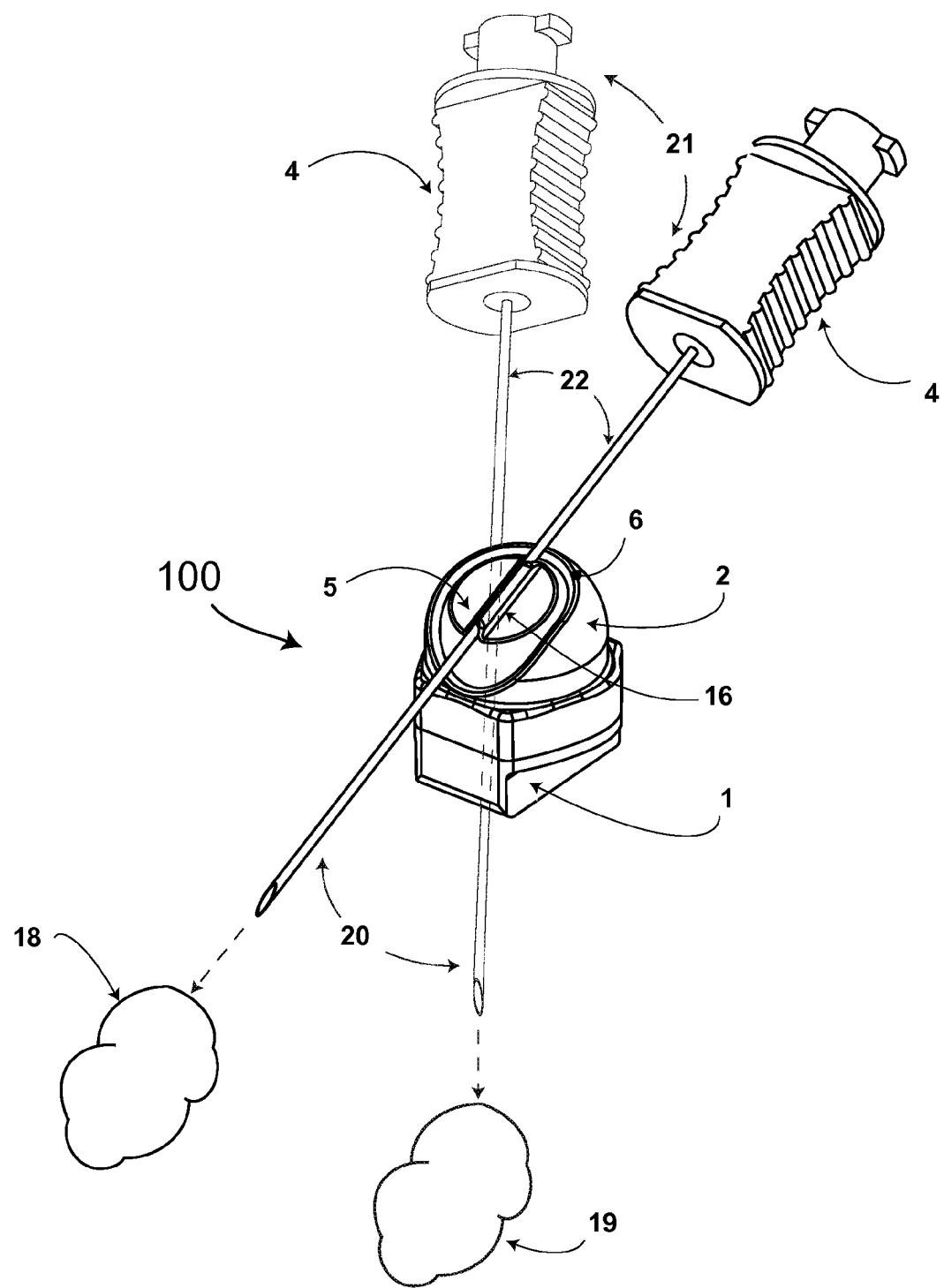
FIG. 10 illustrates an embodiment of a medical instrument guiding device having an integrated guide ball in two different positions.

FIG. 10 illustrates an embodiment of a medical instrument guiding device having an integrated guide ball 100 in two different positions. In a first position, the distal end of a medical instrument 4 is directed toward a first reference position 18. The body base component 1 of the guiding device 100 may be placed proximate a patient (not shown). The guiding device can be placed, for example, on the patient or adjacent to the patient on a support arm or other structure (not shown) that is coupled at surfaces 13a-13c. The distal end of medical instrument 4 may be advanced closer or moved further to the first reference position 18 by applying axial pressure along the main axis of the instrument 4 at the proximal end of medical instrument 4. The medical instrument 4 is passed through the port 5. The clamping structure 16 is formed or adjusted to provide a selected level of friction on the medical instrument 4 as the instrument is moved axially. In a second position, the distal end of the medical instrument 4 is directed toward a second reference position 19. The ball 3 is rotated on the surface 9 (FIGS. 3, 5) and within the upper component 2 as held by the bearing surface 12. A medical practitioner has moved the proximal end of the medical instrument 4 in three dimensions. The medical practitioner may have also rotated the medical instrument 4. The angular displacement of the medical instrument 4 between the first reference position 18 and the second reference position 19 is illustrated in the x-axis 20, the y-axis 21, and the z-axis 22. The full range of angular displacement is limited only by the exposed working area 6. The size and shape of the opening 6 is selected based on the range of expected motion for the medical instrument 4 to be placed therein.

The ball 3 can be rotated by a physician to any desired position, thus changing the orientation and location in the x, y, and z axis of the medical instrument 4. The medical instrument 4 can be advanced or retracted through the port 5.

The operation of the integrated guide ball 100 is as follows. The guide ball 3 is rotatable independently about all axes as it rests on support surface 9 (FIGS. 3, 5). Thus, a medical instrument 4 that extends through the port 5 can be rotated independently about its pitch, yaw, or roll axis. The orientation of the medical device 4 can therefore be moved to any desired position under the control of a physician. The size and shape of the cutout 6 determines the limits of movement. As would be appreciated, generally the medical instrument 4 will be directed to a patient who is positioned below the location of the integrated guide ball assembly 100 and therefore, permits a wide range of movement with the medical instrument 4 pointed in the downward direction, having a larger cutout in the downward part of the sphere than in the upper part. Of course, the cutout 6 could be any shape and could be quite large, to permit rotation of the port 5 to any position, for example, so that a medical instrument 4 therein pointed exactly sideways or upward if such uses were needed for the medical procedure to be performed by the medical instrument 4 mounted therein.

During use, a medical instrument 4 is advanced into the port 5 and has a distal end extending slightly out of the port 5. A physician thereafter rotates the ball 3 to his desired position in order to prepare to carry out a medical procedure. After the ball 3 is held in the desired position, with the medical instrument properly aligned with the target tissue in the body, the physician then advances the medical instrument 4, usually to enter the body of the patient at a desired location and to perform a medical procedure. After the medical instrument 4 enters the body of the patient, it will generally be desired to hold the ball 3 at a rigid or solid position. In one embodiment, the friction between the rotatable ball 3 and the support surface 9 and housing 12 is sufficient that the ball 3 is held in a rigid position unless force to move it is applied by a physician. Thus, the friction between the rotatable ball and the housing is sufficient such that in the absence of a strong external force, the rotatable ball will not move. Thus, in this embodiment, the physician may confidently advance the medical instrument 4 into a patient and be assured that, unless he applies a rotational force to the ball 3, it will remain in the same fixed orientation and not change the orientation of the medical instrument 4 in the body of the patient. In this embodiment, the friction force to hold ball 3 is positioned the same over all uses of the device 100 and does not change. In an alternative design, as will now be explained, the friction between the rotatable ball 3 and the support surface 9 and housing 12 can be varied so as to increase the friction and more rigidly clamp the ball 3 in the device after it has been advanced into the body of the patient, increasing the safety factor during the medical procedure. The clamping force on the alternative ball 3 can be increased by compressing an inner surface of the bearing surface 12, thus rigidly fixing the ball 3 in a fixed position to avoid the orientation of the tip from changing after the medical instrument 4 has been advanced a certain distance into the body. With the ball 3 solidly clamped in a fixed position, the medical instrument 4 can be advanced farther to any desired depth, into the body of the patient and, if desired, the medical instrument 4 can be clamped in the port 5 in order to hold it at a fixed depth inside the body of the patient. It may thus be held positioned at a fixed location in the body of the patient while additional medical procedures are carried out, such as the delivery of therapeutic medication, the removal of tumor cells in the body, the advancing of a catheter inside a lumen of the needle, or any other number of many medical procedures which may be done by the appropriate medical instrument 4.

Accordingly, in one embodiment, the bearing surface 12 permits the physician to freely rotate the ball 3 at some time during the medical procedure in order to properly orient and align the medical instrument 4 and then, at a later point in the procedure, clamp the bearing surface 12 on the ball 3 in order to prevent it from further rotation once the medical instrument 4 is held at the desired orientation.

According to yet a further embodiment, the port 5 may also swivel on top of ball 3. Namely, the physician may clamp the ball 3 to a rigid location and then, in the alternative embodiment, swivel the port 5 about an axis that extends through the center of the ball 3 so as to change the direction which the medical instrument 4 is pointing, but not its height or vertical orientation. Thus, in a first embodiment, the port 5 is rigidly and fixedly attached to the ball 3 and movement of the ball is the only technique by which the orientation of the medical instrument 4 can be varied. In a further alternative embodiment, however, an additional degree of freedom is provided to permit rotation of the port 5 once the ball 3 has been clamped so that some minor movement in one direction can be permitted once the ball 3 is clamped in a fixed position.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A medical instrument guiding device, comprising:
   a body base component;
   a guide body upper component, the guide body upper component coupled to the body base component, the guide body upper component having a substantially semi-spherical shape including a cut out working area within the substantially semi-spherical shape;
   a medical instrument guide ball resting on a friction surface located within the body base component, the medical instrument guide ball having a truncated planar surface exposed by the cut out working area; and
   a medical instrument port arranged upon the exposed truncated planar surface of the medical instrument guide ball, the medical instrument port configured to receive a medical instrument, the medical instrument port arranged to permit line-of-sight exposure of both a proximal end of the medical instrument and a distal end of the medical instrument as the distal end of the medical instrument enters the body of the patient.

2. The medical instrument guiding device of claim 1, further comprising:
   a medical instrument passing through the medical instrument port.

3. The medical instrument guiding device of claim 1, further comprising:
a plurality of joining structures configured in a recess formed in the body base component, the plurality of joining structures including a least one dimple.

4. The medical instrument guiding device of claim 1, further comprising:
a medical instrument clamping structure integrated with the medical instrument port, the medical instrument clamping structure configured to permit manual adjustment of the amount of friction applied on a medical instrument.

5. The medical instrument guiding device of claim 1 wherein the friction surface is formed from a material that is different from the surface of the medical instrument guide ball.

6. A method of providing therapy to a patient, comprising:
placing a body base component of a medical instrument guiding device proximate to a body of the patient;
directing a distal end of a medical instrument toward a selected position, the medical instrument passing through a port arranged upon a truncated planar surface of a medical instrument guide ball, the medical instrument guide ball housed in a cavity formed by the body base component and a semi-spherical guide body upper component;
applying axial pressure to a proximal end of the medical instrument to cause the distal end of the medical instrument to advance into the body of the patient, the medical instrument guiding device arranged to permit line-of-sight exposure of both the proximal end of the medical instrument and the distal end of the medical instrument as the distal end of the medical instrument enters the body of the patient; and
removing axial pressure from the proximal end of the medical instrument to cause the distal end of the medical instrument to remain stationary.

7. The method of providing therapy of claim 6, further comprising:
maneuvering the distal end of the medical instrument in three dimensions, the maneuvering limited by a cut out working area formed in the semi-spherical guide body upper component.

8. The method of providing therapy of claim 6, further comprising:
manually adjusting a clamping structure integrated with the port to cause a change to an amount of friction applied to the medical instrument.

9. The method of providing therapy of claim 6, further comprising:
manually adjusting the semispherical guide body upper component to cause a change to an amount of friction applied to the medical instrument guide ball.

10. The method of providing therapy of claim 6, further comprising:
mounting the body base component on a secondary medical device.

11. A device to guide a medical instrument into a body of a patient, comprising:
a medical instrument guide ball configured to rest on a friction surface within a substantially semi-spherical cavity of a support structure, the medical instrument guide ball having an exposed truncated planar surface; and
a medical instrument port arranged upon the exposed truncated planar surface of the medical instrument guide ball, the medical instrument port configured to receive a medical instrument, the medical instrument port arranged to permit line-of-sight exposure of both a proximal end of the medical instrument and a distal end of the medical instrument as the distal end of the medical instrument enters the body of the patient.

12. The device to guide the medical instrument into the body of the patient of claim 11 wherein the medical instrument port is further arranged to permit guidance of the medical instrument in an orientation substantially parallel to the truncated planar surface.

13. The device to guide the medical instrument into the body of the patient of claim 11, comprising:
a base component forming the support structure, the base component having the substantially semi-spherical cavity, the base component having a planar lower surface.

14. The device to guide the medical instrument into the body of the patient of claim 11, comprising:
a medical instrument passing through the medical instrument port.

15. The device to guide the medical instrument into the body of the patient of claim 11, comprising:
a medical instrument clamping structure integrated with the medical instrument port, the medical instrument clamping structure configured to permit manual adjustment of friction applied to the medical instrument.

16. The device to guide the medical instrument into the body of the patient of claim 11 wherein the medical instrument port includes a substantially cylindrical structure rising above the truncated planar surface.

17. The device to guide the medical instrument into the body of the patient of claim 16 wherein the substantially cylindrical structure is formed as a segmented channel.

18. The device to guide the medical instrument into the body of the patient of claim 11 wherein the medical instrument port includes a pathway for a medical instrument that is biased in a closed orientation, the pathway biased in the closed orientation, a diameter of the pathway being smaller than a diameter of the medical instrument.

* * * * *